US011478780B2

(12) United States Patent
Herzfeld et al.

(10) Patent No.: US 11,478,780 B2
(45) Date of Patent: Oct. 25, 2022

(54) BIMETALLIC NANOPARTICLE-BASED CATALYST, ITS USE IN SELECTIVE HYDROGENATION, AND A METHOD OF MAKING THE CATALYST

(71) Applicant: SHELL OIL COMPANY, Houston, TX (US)

(72) Inventors: Tobias Herzfeld, Leuna (DE); Andreas Klemt, Leuna (DE); Sven Scholz, Leuna (DE)

(73) Assignee: SHELL USA, INC., Houston, TX (US)

(*) Notice: Subject to any disclaimer, the term of this patent is extended or adjusted under 35 U.S.C. 154(b) by 0 days.

(21) Appl. No.: 16/743,693

(22) Filed: Jan. 15, 2020

(65) Prior Publication Data

US 2020/0230580 A1    Jul. 23, 2020

Related U.S. Application Data

(60) Provisional application No. 62/793,561, filed on Jan. 17, 2019.

(51) Int. Cl.
*B01J 21/04* (2006.01)
*B01J 21/06* (2006.01)
(Continued)

(52) U.S. Cl.
CPC .............. *B01J 23/66* (2013.01); *B01J 23/44* (2013.01); *B01J 35/023* (2013.01); *B01J 35/08* (2013.01);
(Continued)

(58) Field of Classification Search
CPC ... B01J 21/04; B01J 21/06; B01J 21/08; B01J 21/10; B01J 21/12; B01J 21/14;
(Continued)

(56) References Cited

U.S. PATENT DOCUMENTS 2,802,889 A    8/1957 Frevel
2,857,337 A   10/1958 Hamilton et al.
(Continued)

FOREIGN PATENT DOCUMENTS

CA    610337 A    12/1960
CN   1361231 A     7/2002
(Continued)

OTHER PUBLICATIONS

Lee et al., "The Distribution of Active ingredients in Supported Catalysts Prepared by Impregnation", Catalysis Reviews, vol. 27, Issue No. 2, 1985, pp. 207-340, XP008097790.
(Continued)

*Primary Examiner* — Cam N. Nguyen
(74) *Attorney, Agent, or Firm* — Shell USA, Inc.

(57) ABSTRACT

Presented is a selective hydrogenation catalyst and a method of making the catalyst. The catalyst comprises a carrier containing bi-metallic nanoparticles. The nanoparticles comprise a silver component and a palladium component. The catalyst is made by incorporating an aqueous dispersion of the bi-metallic nanoparticles onto a catalyst carrier followed by drying and calcining the carrier having incorporated therein the dispersion. The catalyst is used in the selective hydrogenation of highly unsaturated hydrocarbons contained olefin product streams.

28 Claims, 4 Drawing Sheets

(51) Int. Cl.
| | |
|---|---|
| *B01J 21/08* | (2006.01) |
| *B01J 21/10* | (2006.01) |
| *B01J 21/12* | (2006.01) |
| *B01J 23/44* | (2006.01) |
| *B01J 23/50* | (2006.01) |
| *B01J 23/66* | (2006.01) |
| *B01J 35/02* | (2006.01) |
| *B01J 35/08* | (2006.01) |
| *B01J 37/02* | (2006.01) |
| *C10G 45/34* | (2006.01) |
| *B82Y 30/00* | (2011.01) |
| *B82Y 40/00* | (2011.01) |

(52) U.S. Cl.
CPC ....... *B01J 37/0201* (2013.01); *B01J 37/0236* (2013.01); *C10G 45/34* (2013.01); *B82Y 30/00* (2013.01); *B82Y 40/00* (2013.01); *C10G 2400/22* (2013.01)

(58) Field of Classification Search
CPC ... B01J 23/44; B01J 23/50; B01J 23/66; B01J 37/0201; B01J 37/0236; B01J 35/023; B01J 35/08
See application file for complete search history.

(56) References Cited

U.S. PATENT DOCUMENTS

| | | | |
|---|---|---|---|
| 3,243,387 A | 3/1966 | Blume et al. | |
| 4,329,530 A | 5/1982 | Irvine et al. | |
| 4,484,015 A | 11/1984 | Johnson et al. | |
| 4,762,956 A | 8/1988 | Liu et al. | |
| 5,510,550 A | 4/1996 | Cheung et al. | |
| 5,585,318 A | 12/1996 | Johnson et al. | |
| 5,889,187 A | 3/1999 | Nguyen Than et al. | |
| 5,900,386 A | 5/1999 | Freund et al. | |
| 6,084,140 A | 7/2000 | Kitamura et al. | |
| 6,255,548 B1 | 7/2001 | Didillon et al. | |
| 6,350,717 B1 | 2/2002 | Frenzel et al. | |
| 6,417,136 B2 | 7/2002 | Cheung et al. | |
| 6,572,673 B2 | 6/2003 | Lee et al. | |
| 6,603,038 B1* | 8/2003 | Hagemeyer | B01J 23/38 502/325 |
| 6,797,669 B2 | 9/2004 | Zhang et al. | |
| 6,987,200 B2* | 1/2006 | Hagemeyer | B01J 23/38 560/245 |
| 7,301,062 B2 | 11/2007 | Gartside et al. | |
| 7,453,017 B2 | 11/2008 | Moon et al. | |
| 7,521,393 B2 | 4/2009 | Blankenship et al. | |
| 7,998,247 B2 | 8/2011 | Saukaitis et al. | |
| 8,030,242 B2* | 10/2011 | Uzio | C10G 2/331 502/325 |
| 8,067,334 B2 | 11/2011 | Hill et al. | |
| 8,158,837 B2 | 4/2012 | Mamadov et al. | |
| 8,652,232 B2* | 2/2014 | Bisson | B22F 9/26 75/371 |
| 8,822,725 B2 | 9/2014 | Witte | |
| 9,283,545 B2* | 3/2016 | Asefa | B01J 35/0086 |
| 9,878,306 B2* | 1/2018 | Qin | B01J 23/50 |
| 10,286,382 B2* | 5/2019 | Qin | B01J 35/06 |
| 10,456,838 B2* | 10/2019 | Choi | B22F 1/0018 |
| 10,543,536 B2* | 1/2020 | Kim | B22F 1/0044 |
| 10,906,033 B2* | 2/2021 | Hua | B01J 31/061 |
| 10,960,470 B2* | 3/2021 | Humphrey | C22C 5/02 |
| 2003/0134744 A1 | 7/2003 | Blankenship et al. | |
| 2003/0187294 A1* | 10/2003 | Hagemeyer | B01J 23/52 560/241 |
| 2004/0248732 A1 | 12/2004 | Cheung et al. | |
| 2005/0137433 A1 | 6/2005 | Bergmeister, III et al. | |
| 2006/0107424 A1 | 5/2006 | Colbert et al. | |
| 2007/0027030 A1 | 2/2007 | Cheung et al. | |
| 2009/0226357 A1* | 9/2009 | Uzio | C10G 2/331 423/437.2 |
| 2010/0200501 A1* | 8/2010 | Hoag | B82Y 30/00 210/620 |
| 2010/0280296 A1* | 11/2010 | Bisson | C10G 45/34 585/277 |
| 2012/0055873 A1* | 3/2012 | Hoag | B22F 9/24 210/633 |
| 2015/0314269 A1* | 11/2015 | Carpenter | B01J 37/024 502/243 |
| 2016/0136632 A1* | 5/2016 | Monnier | C07C 17/08 502/182 |
| 2016/0221028 A1 | 8/2016 | Alitalo et al. | |
| 2017/0368535 A1* | 12/2017 | Chopra | B01J 35/002 |
| 2018/0117566 A1 | 5/2018 | Witte et al. | |
| 2018/0147563 A1 | 5/2018 | Boualleg et al. | |

FOREIGN PATENT DOCUMENTS

| | | |
|---|---|---|
| CN | 1544145 A | 11/2004 |
| DE | 1171901 B | 6/1964 |
| DE | 3543640 A1 | 6/1987 |
| DE | 19757990 A1 | 7/1998 |
| FR | 2603578 A1 | 3/1988 |
| GB | 686574 A | 1/1953 |
| GB | 1133253 A | 11/1968 |
| JP | S5211185 A | 1/1977 |
| JP | S54157507 A | 12/1979 |
| JP | S5817835 A | 2/1983 |
| KR | 20000059743 A | 10/2000 |
| WO | 2008127406 A2 | 10/2008 |
| WO | 2011113881 A1 | 9/2011 |
| WO | 2013186789 A1 | 12/2013 |

OTHER PUBLICATIONS

International Search Report and Written Opinion received for PCT Patent Application No. PCT/EP2011/054011, dated Oct. 12, 2011, 09 pages.

* cited by examiner

BIMETALLIC NANOPARTICLE-BASED CATALYST, ITS USE IN SELECTIVE HYDROGENATION, AND A METHOD OF MAKING THE CATALYST

This application claims the benefit of U.S. Provisional Patent Application 62/793,561 filed Jan. 17, 2019 entitled BIMETALLIC NANOPARTICLE-BASED CATALYST, ITS USE IN SELECTIVE HYDROGENATION, AND A METHOD OF MAKING THE CATALYST, the entirety of which is incorporated by reference herein.

This invention relates to a catalyst composition that includes bi-metallic nanoparticles contained on a carrier and a method of making the catalyst composition. The catalyst composition is useful in the selective hydrogenation of highly unsaturated hydrocarbons contained in a treatment stream of less unsaturated hydrocarbons.

BACKGROUND OF THE INVENTION

Steam crackers and refinery cracking units provide for production of unsaturated hydrocarbon product streams that are used as feedstocks for downstream processes and in other applications. Steam crackers typically crack lower molecular weight saturated hydrocarbons, such as ethane, propane, and butane, or naphtha boiling range hydrocarbons to yield lighter alkenes, such as ethylene, propylene, and butylene. Refinery cracking units typically crack heavier hydrocarbon fractions to yield multiple product streams among which are lighter gaseous hydrocarbons having high concentrations of unsaturated hydrocarbons.

One problem with the light olefin product streams yielded from these cracking units is that the olefin product streams may contain unacceptable concentrations of more highly unsaturated hydrocarbons. For example, an ethylene product stream can have a contaminating concentration of acetylene, or a propylene product stream can have contaminating concentrations of methylacetylene (MA) and propadiene (PD). The acetylene contained in the ethylene product stream, and the methylacetylene and propadiene contained in the propylene product stream need to be removed from these products for them to be useable.

Thus, the highly unsaturated hydrocarbons such as diolefins and hydrocarbons having triple bonds (alkynes) need to be removed from the less unsaturated product streams such as ethylene or propylene product streams. Selective hydrogenation processes typically are used to remove undesired highly unsaturated hydrocarbons from less unsaturated hydrocarbon streams.

The selective hydrogenation process is a catalytic process. This process includes contacting under suitable reaction conditions an olefin stream having a concentration of more highly unsaturated hydrocarbons with a selective hydrogenation catalyst. The more highly unsaturated hydrocarbons are selectively hydrogenated to olefins with a minimal amount of hydrogenation of the desirable olefins of the olefins streams. Desirable characteristics of the selective hydrogenation catalyst is that it has high activity for providing the described selective hydrogenation and it exhibits a long operating life.

PCT publication, WO 2013/186789, describes one of these selective hydrogenation catalysts. This catalyst comprises an inorganic oxide carrier and so-called fine-alloy particles of an active metal component and a promoter component. The active metal is selected from palladium, platinum and nickel, and the promoter is selected from silver, gold and copper. The fine-alloy particles are dispersed onto the surface of the inorganic oxide carrier by the con-current dispersion process, which employs an equilibrium absorption impregnation of the inorganic oxide carrier by contacting it with a solution comprising the fine alloy particles.

The fine alloy particles are prepared by dissolving an active metal precursor, e.g., a palladium salt, and a promoter metal precursor, e.g., a silver salt, in an aqueous acidic solution. These precursors are dissolved in water with the pH controlled within the range of from 1.2 to 1.4. The aqueous acidic solution is heated and maintained for a time-period at a temperature of about 70° C.

No surfactant is used in the preparation of the aqueous acidic solution. There is no indication or suggestion that the fine alloy particles are bi-metallic, core-shell nanoparticles, especially, since no surfactant is used in the preparation of the aqueous acidic solution. The disclosure further fails to present any information on the form or other properties of the fine alloy particles. The specification mentions no components of the aqueous acidic solution other than water, metal precursors, and hydrochloric acid. Thus, none of the typically known reducing agents are used in the preparation of the aqueous acidic solution.

The catalyst of WO 2013/186789 is prepared by impregnating the inorganic oxide carrier with the aqueous acidic solution of fine alloy particles followed by drying and calcining the impregnated carrier to provide the final catalyst. A required property of the catalyst is that the palladium is dispersed on at least 30% of the surface area of the inorganic oxide carrier as measured by the $H_2$ Chemisorption method.

U.S. Pat. No. 6,572,673 is a related publication because it discloses a method of preparing noble metal nanoparticles. The '673 disclosure mentions that its noble metal nanoparticles have application in electroless plating of electronic circuits and as a catalyst for catalyzing the reaction of unsaturated hydrocarbons. The nanoparticles are prepared by reacting a noble metal salt and an anionic surfactant in the absence of added reducing agent and at a temperature in the range of from 50 to 140° C.

The '673 patent, however, does not mention bi-metallic nanoparticles, and, particularly, it fails to teach anything about bi-metallic nanoparticles having a core-shell structure. There also is no teaching of catalyst compositions made by impregnation of an inorganic oxide carrier with a dispersion of noble metal nanoparticles or of any type of supported catalyst composition.

BRIEF SUMMARY OF THE INVENTION

It is an object of the invention to provide an improved selective hydrogenation catalyst.

Accordingly, provided is a composition useful as a selective hydrogenation catalyst or selective hydrogenation catalyst precursor. The composition comprises a carrier containing bi-metallic nanoparticles. The bi-metallic nanoparticles of the composition comprise a silver component and a palladium component.

The inventive selective hydrogenation catalyst is prepared by providing an aqueous dispersion of bi-metallic nanoparticles formed by the reduction of a palladium salt and a silver salt in a mixture by the application of a surfactant. The aqueous dispersion is incorporated into a carrier to provide an impregnated carrier that is dried followed by calcination at a low calcination temperature to provide the catalyst composition.

BRIEF DESCRIPTION OF THE FIGURES

This specification provides the following figures to help describe and illustrate the invention.

DETAILED DESCRIPTION OF THE INVENTION

Figure 1:
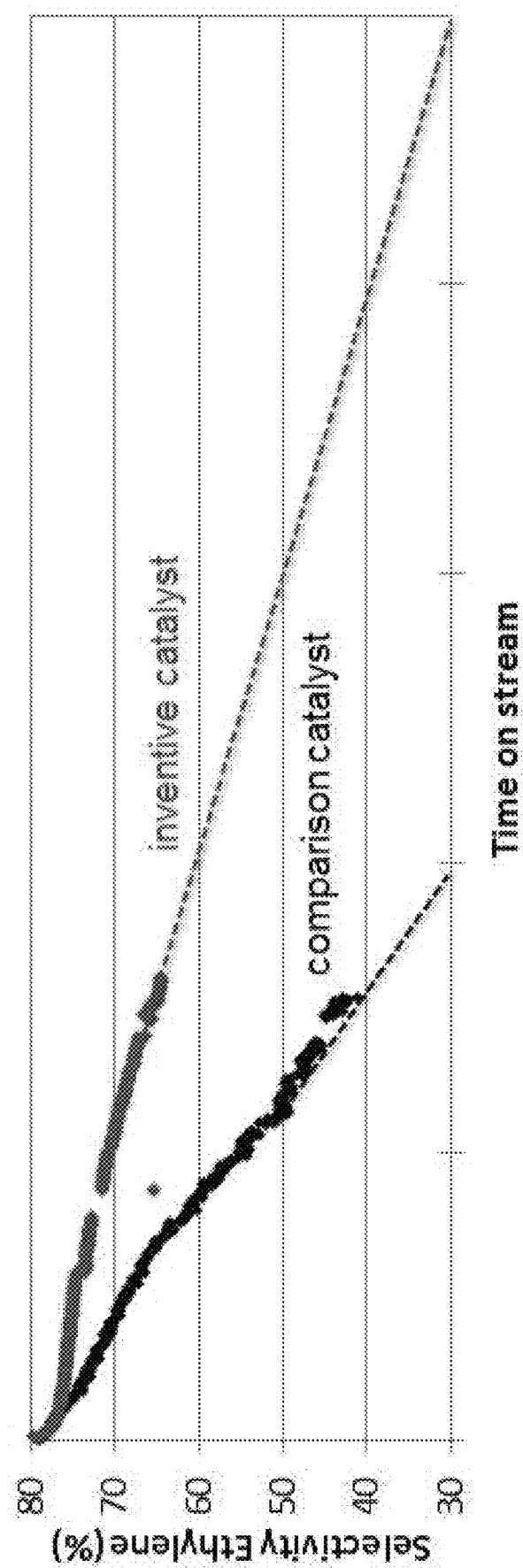
FIG. 1 presents plots of catalyst selectivity versus time-on-stream (TOS) for the inventive catalyst and a comparison catalyst.

Presented in this specification is a novel catalyst composition that is useful in the selective catalytic hydrogenation of highly unsaturated hydrocarbons contained at contaminating levels in olefin process streams containing olefin hydrocarbons.

The application of the inventive catalyst composition includes contacting under suitable reaction conditions an olefin process stream, which may have a concentration of highly unsaturated hydrocarbons, with the catalyst. The catalyst provides for selective hydrogenation of the highly unsaturated hydrocarbons to less unsaturated hydrocarbons, i.e., olefins, but with a minimum amount of undesirable hydrogenation of the olefins of the olefin process stream. Indeed, when referring in this specification to the selective hydrogenation catalyst of the invention, what is meant is that the catalyst provides for the hydrogenation of highly unsaturated hydrocarbons, such as alkynes and diolefins, contained in the olefin stream without hydrogenating a significant amount of an olefins in the olefin stream to saturated hydrocarbons.

The inventive catalyst is highly selective, particularly, when used in the selective hydrogenation of acetylene contained in ethylene process streams. The catalyst also is very stable in that the rate of decline in its selectivity and activity with time-on-stream (TOS) is much lower than that of other comparative catalysts. This means that the cycle length of the catalyst in use is much longer than the cycle length for other comparative catalysts. In fact, the inventive catalyst can provide for a cycle length as much as twice that for other catalysts.

The unexpectedly high selectivity characteristic of the inventive catalyst provides for a much lower yield of undesirable green oil by-product when used the catalyst is used in the selective hydrogenation process. "Green oil" refers to a mixture of compounds produced by side reactions during the selective hydrogenation of alkynes and diolefins contained in the olefin process stream. These side reactions form dimers, trimers and other oligomers of the alkynes and diolefins. The green oil oligomer compounds can have up to 16 or more carbon atoms per molecule.

The inventive composition is a selective hydrogenation catalyst or selective hydrogenation catalyst precursor that can provide the numerous benefits discussed in this specification. This composition comprises a carrier that contains bi-metallic nanoparticles. The bi-metallic nanoparticles comprise a silver component and a palladium component.

It is believed that the morphology and other characteristics of the bi-metallic nanoparticles used to prepare the catalyst composition of the invention significantly contribute its special properties. One such characteristic of the bi-metallic nanoparticles is the high surface area-to-volume ratio of the particles. The smaller nanoparticles have higher surface area-to-volume ratios than the larger particles. These higher surface area-to-volume ratios contribute to the improved catalytic properties of the inventive selective hydrogenation catalyst. Thus, it is desirable for the bi-metallic nanoparticles of the inventive catalyst to have the highest surface area-to-volume ratio as is feasible.

The nanoparticles are dispersed on the surface of the carrier of the catalyst and generally have a particle size distribution such that at least 80 percent, but, more preferably, at least 90 percent of the bi-metallic nanoparticles are of a size within the range of from 1 nanometer (nm) to 10 nm. The size distribution of the bi-metallic nanoparticles also can approximate a Gaussian distribution with the mean particle size within the range of from 1 nm to 10 nm and a standard deviation ($\sigma$) in the range of from 0.1 to 2.5. The bi-metallic nanoparticles can be characterized by using a transmission electron microscope (TEM) or by the Dynamic Light Scattering method.

In addition to the size of the bi-metallic nanoparticles, there are other characteristics of the nanoparticles that in combination with the particle size contribute to the unexpected properties of the inventive catalyst composition. Among these is the relative amounts of silver and palladium metals contained in the nanoparticles. This ratio can be an important contributor to the selectivity of the catalyst. In all instances, the palladium-to-silver molar ratio of the bi-metallic nanoparticle should be within the range of from 0.01:1 to 100:1. But, it is preferred for the silver and palladium to be present in the bi-metallic nanoparticles at a palladium-to-silver molar ratio within a much narrower range. Particularly, the molar ratio of palladium-to-silver in the bi-metallic nanoparticles is in the range of from 0.01 to 10:1. Preferably, however, the palladium-to-silver ratio is in the range of from 0.1:1 to 5:1. It is more preferred for the palladium-to-silver ratio to be within the range of from 0.1:1 to 3:1, and, most preferred, it is from 0.2:1 to 2:1.

The bi-metallic nanoparticles may have several forms which include particles that are alloys of silver and palladium and particles having a core-shell structure with one metal component forming the core of the particle and the other metal component forming a shell that surrounds the core.

Regarding the core-shell structure form of the bi-metallic nanoparticles, the access of reaction molecules to the different metal components of the nanoparticles can be influenced by their core-shell structure. For example, if the palladium metal component of the particle forms the shell and the silver metal component of the particle forms the core, reaction molecules have easier or more ready access to the palladium metal of the shell than to the silver metal of the core. The reaction can be influenced by the relative difference in access by the reaction molecules to the different metals of the bi-metallic nanoparticles.

The core-shell structure of the bi-metallic nanoparticles comprises an inside core, having first major portion of a first metal component, and an outer shell, having a second major portion of a second metal component that surrounds the core. While neither the geometric shape of the bi-metallic nanoparticles nor their inside cores are perfectly spherical, they are approximately spherical in shape.

The core-shell bi-metallic nanoparticles are, thus, characterized herein as two concentric spheres, including an overall sphere-shaped nanoparticle having an outside diameter ($D_o$) that encompasses an inside spherical core having a core diameter ($D_i$), wherein $D_o$ is greater than $D_i$ with the region between the two spheres defining an outer shell that surrounds the inside spherical core. The outer shell has a shell thickness ($\Theta$). The shell thickness, $\Theta$, approximates the difference between the outside diameter, $D_o$, of the spherical particle and the diameter, $D_i$, of the inside core divided by 2, i.e., $\Theta=[(D_o-D_i)/2]$. The ratio of shell thickness-to-outside diameter, i.e., $\Theta/D_o$, of the bi-metallic nanoparticles having the core-shell structure is in the range of from 0.01 to 0.8 (1% to 80%). The preferred ratio, however, is in the range of from 0.03 to 0.6 (3% to 60%), and, more preferred, the ratio is in the range of from 0.05 to 0.4 (5% to 40%).

The first metal component of the core of the bi-metallic nanoparticles may be either silver or palladium and the second metal component of the outer shell of the bi-metallic nanoparticles may be either palladium or silver. If the first metal component of the inside core is silver, then palladium is the second metal component of the outer shell. Alternatively, if the first metal component of the inside core is palladium, the silver is the second metal component of the outer shell.

The bi-metallic nanoparticles of the inventive catalyst are prepared by the method described in this specification. This method provides an aqueous dispersion of the nanoparticles used in the preparation of the catalyst. The catalyst preparation includes incorporating the aqueous dispersion of bi-metallic nanoparticles into a shaped inorganic oxide carrier dispersing the bi-metallic nanoparticles onto the surface of the shaped inorganic oxide carrier that is thereafter dried and calcined to provide the catalyst.

Incorporation of the aqueous dispersion of bi-metallic nanoparticles onto the shaped inorganic oxide carrier results in dispersing the bi-metallic nanoparticles on the surface of the shaped inorganic oxide carrier. The resulting metal surface area as can be measured by $H_2$ Chemisorption is less than 25% of the BET surface area of the shaped inorganic oxide carrier. More typically, it is in the range of from 0.01% to 22%, and, most typically, from 0.02% to 20%.

The $H_2$ Chemisorption method for measuring the dispersion of the nanoparticles on the surface of the shaped inorganic oxide carrier is performed according to ASTM D3908.

The carrier component of the inventive catalyst is prepared by any of the suitable methods known to those skilled in the art for preparing shaped porous catalyst supports used to carry catalytically active metals. The carrier or shaped inorganic oxide carrier comprises a porous refractory oxide or inorganic oxide component such as alumina, silica, alumina-silica, titania, zirconia, boria, magnesia, zeolites and combinations thereof. The preferred inorganic oxide for the shaped inorganic oxide carrier of the catalyst is one selected from the group consisting of alumina, silica, alumina-silica, and titania. Among these, the most preferred inorganic oxide is alumina.

The inorganic oxide of the carrier is formed into a shaped structure by any known suitable method. The extruded shaped structures typically are prepared by mixing an inorganic oxide powder with water and one or more additives to form a mixture having plastic properties and forming the mixture into extrudates by any of the known extrusion methods. The formed extrudates can be cylinders, lobed-shaped, and twisted shapes having nominal extrudate diameters in the range of from 0.5 mm to 25 mm and extrudate lengths in the range of from 1 mm to 50 mm.

Spherically shaped structures or balls of the inorganic oxide carrier can be made by the application of any of the known granulation methods, which use an inclined rotating disk or pan that is fed particles of the inorganic oxide while spraying a cohesive slurry onto the particles. By this method the particles are formed into spherically shaped particles. The spherically shaped carrier particles have diameters in the range of from 0.5 mm to 25 mm Dry tableting methods may also be used to prepare the shaped carrier structure. In this method, cylindrical pellets or pills of the inorganic oxide are made by pressing a dry inorganic oxide powder that is optionally mixed with additives such as a lubricant and a binder, between two punches in a tableting press. Carrier particles that are cylindrical pellets have pellet diameters in the range of from 0.5 mm to 25 mm and pellet lengths in the range of from 1 mm to 50 mm These shaped support particles are then dried under standard drying conditions that can include a drying temperature in the range of from 50° C. to 200° C., preferably, from 75° C. to 175° C., and more preferably, from 90° C. to 150° C.

After drying, the shaped support particle is calcined under standard calcination conditions that include a calcination temperature in the range of from 800° C. to 1,500° C., preferably, from 900° C. to 1,400° C., and, most preferably, from 1,000° C. to 1,300° C.

The shaped support that has been calcined should have a surface area and pore volume that allow for the impregnation of the shaped support with the bi-metallic nanoparticles. The calcined shaped support can have a surface area (determined by the BET method employing $N_2$, ASTM test method D3037) that is in the range of from 1 $m^2/g$ to 100 $m^2/g$, preferably, from 5 $m^2/g$ to 50 $m^2/g$, and, most preferably, from 5 $m^2/g$ to 35 $m^2/g$.

The mean pore diameter in angstroms (Å) of the calcined shaped support is in the range of from 50 to 200, preferably, from 70 to 150, and, most preferably, from 75 to 125.

The pore volume of the calcined shaped support should exceed 0.2 cc/g and is typically in the range of from 0.3 cc/g to 1.1 cc/g. More typically, the pore volume is in the range of from 0.35 cc/g to 0.9 cc/g, and, most typically, it is from 0.4 to 0.7 cc/g.

The references herein to pore size distribution and pore volume of the calcined shaped particle are to those properties as determined by mercury intrusion porosimetry, ASTM test method D 4284. The measurement of the pore size distribution of the calcined shaped particle is by any suitable measurement instrument using a contact angle of 140° with a mercury surface tension of 474 dyne/cm at 25° C.

A preferred attribute of the inventive catalyst is for it to be a so-called eggshell type catalyst with the bi-metallic nanoparticles that are incorporated into the shaped carrier structure deposited and collected predominantly within a thin surface layer near the outer perimeter and surface of the shaped carrier structure. This feature is important, because it contributes to the enhanced selectivity properties of the catalyst. This enhanced selectivity results from combining use of the bi-metallic nanoparticles with their placement near the outer perimeter and surface or surface layer skin of the catalyst carrier. This combination of features provides greater catalytic benefits than the eggshell characteristic alone.

Certain other embodiments of the inventive catalyst include features that contribute to even greater benefits than either the eggshell property alone or the combination of the use of bi-metallic nanoparticles in an eggshell type catalyst. It is a preferred feature of the inventive catalyst that core-shell type bi-metallic nanoparticles of the invention are used in combination with depositing most of the bi-metallic nanoparticles within a skin layer of the outer perimeter and surface of the shaped carrier structure. So, for this embodiment, the bi-metallic nanoparticles of the catalyst are core-shell type, and they are contained in the shaped carrier structure in a manner that provides an eggshell type catalyst composition.

Thus, a preferred embodiment of the inventive catalyst is that it has eggshell type characteristics, wherein the bi-metallic nanoparticles, which are preferably core-shell nanoparticles, reside predominantly within the outer shell region of the shaped carrier structure.

In characterizing the catalyst, the shaped carrier structure defines a particle volume by its outside surface. This specification further characterizes the shaped carrier structure as having an outer shell region and an interior region.

The outer shell region is defined as the peripheral region or outer skin layer having a depth within the particle volume. The inside boundary of the outer shell region may be defined by the terminal points of each vector that extends from each point on the outer surface of the shaped structure perpendicularly from the tangent to each such point inwardly toward the interior of the shaped structure for a vector length or also referred to herein as depth.

The interior region of the shaped carrier structure is the particle volume other than the outer shell region.

The depth of the outer shell region should be in the range of from as small as 20 nm (0.02 µm), approaching the depth of a monolayer of bi-metallic nanoparticles, up to 500 µm (500,000 nm). As described above, it is desirable for the bi-metallic nanoparticles to be concentrated in a thin boundary layer of the shaped carrier structure and thus the depth of the outer shell region should be relatively narrow. Thus, it is preferable for the depth of the outer shell region to be within the range of from 5,000 nm (5 µm) to 400 µm (400,000 nm), and, more preferably, the depth is within the range of from 10,000 nm (10 µm) to 300 µm (300,000 nm).

Important embodiments of the invention are the methods by which the bi-metallic nanoparticles are prepared and incorporated into the carrier of the catalyst. It is the specific method by which the bi-metallic nanoparticles are made that provides particles having the necessary characteristics which contribute to the enhanced properties of the inventive selective hydrogenation catalyst. The inventive catalyst is prepared by incorporating into its carrier an aqueous dispersion of the bi-metallic nanoparticles made by the method described herein.

The aqueous dispersion of bi-metallic nanoparticles is prepared by mixing in water a salt of palladium metal, a salt of silver metal, and a surfactant. This mixture is heated at a low temperature, preferably while stirring the mixture, for a sufficient time to allow the formation of the bi-metallic nanoparticles and the dispersion of the particles within the aqueous phase of the aqueous dispersion.

One important feature of this preparation method is that the surfactant has bifunctional properties providing for both the reduction of the palladium and silver ions to the metals and the dispersion of the formed nanoparticles. Thus, one difference this method has over many other methods of preparing metal nanoparticles described in the art is that it does not use an additional separate reducing agent. Instead, the surfactant acts as the reducing agent. Due to the dual function of the surfactant used in the preparation of the aqueous dispersion of palladium and silver nanoparticles, an embodiment of the invention includes the preparation of the mixture that comprises a silver salt, a palladium salt, a surfactant, and water but having a material absence of a separately added reducing agent. There should be no addition of a separate reducing agent to the mixture during it preparation.

Another of the differences of this preparation method over other methods is the formation of the bi-metallic nanoparticles, particularly, palladium and silver nanoparticles, as opposed to the formation of single metal nanoparticles. In preparing the aqueous mixture of palladium salt, silver salt and surfactant, the relative amounts of metal salts mixed together are to provide nanoparticles having the desired palladium-to-silver molar ratios as discussed in this specification. The aqueous mixture will also have metal concentrations so that when the aqueous dispersion is incorporated into the catalyst carrier the final catalyst has the metal concentrations as discussed in the specification.

It is believed that the surfactant used in the preparation of the aqueous dispersion of bi-metallic nanoparticles provides for the formation of the unique core-shell nanoparticles of the invention. In the preparation of the aqueous mixture of metal salts and surfactant, spherical micelles are formed with the surfactant acting as both a stabilizer and a reducing agent. The mixture is heated at a low temperature for time sufficient to reduce the two metals and to form the bi-metallic nanoparticles. During the heating of the mixture, a portion of the surfactant is hydrolyzed causing the release of a reducing compound. The reduced metals accumulate in the center of the micelles and form the nanoparticles. The rate of reduction of the two metals, however, is different for each of them. This difference in their reduction rate contributes to the formation of the core-shell structure of the nanoparticles.

The heating of the mixture is conducted at a low temperature in the range of from 30° C. to 120° C. Preferably, the heating temperature is in the range of from 40° C. to 110° C., and, more preferably, from 50° C. to 100° C. The heating temperature is important to the nanoparticle preparation. A too high temperature will cause too much of the surfactant to hydrolyze. If the temperature is too low, the nanoparticles will not properly form.

One benefit provided by the nanoparticle preparation method of the invention is that it accelerates the reduction of the metals and shortens the heating time required to achieve the reduction of the metals and formation of the nanoparticles. The mixture is heated for a time sufficient to provide for nanoparticle formation, which should be no longer than 10 hours. The heating time, however, is preferably in the range of from 0.1 hour to 8 hours, and, more preferably, from 0.2 hour to 6 hours.

The pH of the aqueous dispersion of bi-metallic nanoparticles is typically set by the components used in its preparation and is generally less than 9. More typically, the pH is in the neutral or acidic pH ranges, such as acidic to or about 7. Most typically, the pH is in the range of from 1 to 5 or 6.

The silver salt used in the preparation of the aqueous dispersion of bi-metallic nanoparticles of the invention is selected from the group of silver salts consisting of silver nitrate, silver halide, silver carbonate, silver phosphate, silver acetate, silver hydroxide, silver oxide, and silver sulfate. The preferred silver salt is silver nitrate.

The palladium salt used in the preparation of the aqueous dispersion of bi-metallic nanoparticles of the invention is selected from the group of palladium salts consisting of palladium nitrate, palladium halide, palladium carbonate, palladium phosphate, palladium acetate, palladium oxide and palladium sulfate. The preferred palladium salt is palladium nitrate.

The surfactant used in the preparation of the aqueous dispersion of bi-metallic nanoparticles of the invention can be any suitable cationic, anionic or nonionic surfactant that acts as both a stabilizer and reducing agent, as discussed above, and that provides for the formation of micelles in water within which the bi-metallic nanoparticles are formed or grow.

Suitable anionic surfactants may be selected from the group consisting of organo sulfate compounds, organo sulfite compounds, organo sulfonate compounds, organo phosphate compounds, and organo carboxylate compounds. The preferred surfactant is an organo sulfate compound and among these, sodium dodecyl sulfate is the most preferred surfactant.

Suitable cationic surfactants may be selected from the group surfactant compounds consisting of ammonium salts of primary amines, secondary amines and tertiary amines Examples of cationic surfactants that may be used include quaternary ammonium surfactant compounds, such as, cetrimonium bromide, cetylpyridinium chloride, benzalkonium chloride, benzethonium chloride, dimethyldioctadecylammonium chloride, and dioctadecyldimethylammonium bromide.

Suitable nonionic surfactants may be selected from the group of compounds consisting of ethoxylates, fatty alcohol ethoxylates, alkylphenol ethoxylates, and fatty acid esters. Examples of fatty alcohol nonionic surfactants that may be used include octaethylene glycol monododecyl ether and entaethylene glycol monododecyl ether. Examples of alkylphenol ethyoxylates include the nonoxynols and Triton X-100. Examples of fatty acid esters that can function as nonionic surfactants include glycerol monostearate, glycerol monolaurate, sorbitan monolaurate, sorbitan monostearate, and sorbitan tristearate.

The nanoparticles of the invention are incorporated into the catalyst carrier by any suitable method for dispersing them onto the surface area of the shaped inorganic oxide carrier. As previously noted, the dispersion of the bi-metallic nanoparticles on the surface area of the catalyst carrier should be less than 25% of the surface area of the shaped inorganic oxide carrier as measured by $H_2$ Chemisorption method.

It is preferred to impregnate the shaped inorganic oxide carrier with the aqueous dispersion of bi-metallic nanoparticles by the application of any of the known impregnation methods such as incipient wetness impregnation and wet impregnation. The incipient wetness impregnation is done by contacting the carrier particles with a volume of the impregnation solution, i.e., the aqueous dispersion of bi-metallic nanoparticles, which is essentially equivalent to the total water pore volume of the carrier particles. The wet impregnation method involves contacting the carrier particles by dipping or submerging them in the impregnation solution or passing the impregnation solution over the carrier particle for a defined time-period.

These methods provide for the accumulation of a major portion of the nanoparticles within the outer shell region of the shaped inorganic oxide carrier. Upon contacting the surface of the inorganic oxide carrier with the aqueous dispersion of the bi-metallic nanoparticles, the nanoparticles contained in the aqueous dispersion tend to settle down and collect within the outer shell region of the shaped inorganic oxide carrier. At least 90 wt. % of the nanoparticles, thus, accumulate and lay down within the outer shell region of the shaped carrier structure. Few, if any, of the nanoparticles collect or are deposited on the carrier surface within the interior region of the shaped carrier structure. Depositing of the nanoparticles within the outer shell region of the shaped carrier structure provides for the eggshell characteristic of the inventive catalyst.

The impregnated carrier is dried using conventional drying methods at a drying temperature in the range of from 40° C. to 180° C. Preferably, the drying temperature is within the range of from 50° C. to 160° C., and, more preferably, from 50° C. to 150° C.

After the impregnated carrier is dried, it is then calcined in the presence of oxygen, preferably air, at a calcination temperature in the range of from 250° C. to 600° C. to provide the selective hydrogenation catalyst composition of the invention. Preferably, the calcination temperature is within the range of from 320° C. to 550° C., and, more preferably, from 350° C. to 525° C.

The selective hydrogenation catalyst composition of the invention after incorporation of the nanoparticles into the carrier, drying the impregnated carrier, and calcining the dried carrier has a total silver content in the range of from 0.01 wt. % to 1 wt. % and total palladium content in the range of from 0.01 wt. % to 1 wt. %. Preferably, the total silver content is in the range of from 0.015 wt. % to 0.09 wt. %, and, more preferably, from 0.02 wt. % to 0.08 wt. %. Preferably, the total palladium content of the selective hydrogenation catalyst composition is in the range of from 0.015 wt. % to 0.09 wt. %, and, more preferably, from 0.02 wt. % to 0.08 wt. %. The weight percent silver is based on the total weight of the catalyst composition assuming the silver is metal regardless of its actual form. The weight percent palladium is based on the total weight of the catalyst composition assuming the palladium is metal regardless of its actual form.

The inventive selective hydrogenation process uses the catalyst composition described herein. The selective hydrogenation process may be carried out in a single reactor or more than one reactor connected in any suitable flow arrangement. If more than one reactor is employed, then the reactors may be arranged in parallel flow or series flow or a combination of the two flow arrangements. Each reactor defines a reaction zone that contains a volume of the selective hydrogenation catalyst. The reactors are each equipped with a feed inlet means for receiving and introducing a feed stream into its reaction zone, which is operated at selective hydrogenation reaction conditions. The reactors are also each equipped with a reactor effluent outlet means for withdrawing a reactor effluent from its reaction zone.

In the selective hydrogenation process, an olefin feed is introduced into a reaction zone containing the selective hydrogenation catalyst. The olefin feed is contacted with the catalyst within the reaction zone under selective hydrogenation reaction conditions. The olefin feed is an alkene product stream, which comprises monounsaturated hydrocarbons. The preferred monounsaturated hydrocarbon product streams may be a product stream of either ethylene, or propylene, or butylene, or a combination of these low-molecular weight olefins.

The olefin feed or alkene product stream treated by the selective hydrogen process of the invention can also contain a contaminating concentration of highly unsaturated hydrocarbons, such as an alkyne, e.g., acetylene or methylacetylene, and polyunsaturated hydrocarbons, such as diolefins, e.g., propadiene. The selective hydrogenation catalyst of the invention provides for the selective hydrogenation of the highly unsaturated hydrocarbons contained in the olefin feed to their respective monosaturated hydrocarbon, i.e. olefin, with a minimum amount of hydrogenation of the olefins of the olefin feed to saturated hydrocarbons.

The preferred use of the selective hydrogenation catalyst is in the selective hydrogenation of acetylene contained in an ethylene product stream or the selective hydrogenation of methylacetylene and propadiene contained in a propylene product stream. Of these two processes, the selective hydrogenation catalyst of the invention is particularly useful in the selective hydrogenation of acetylene contained in an ethylene product stream.

The ethylene product feed to the selective acetylene hydrogenation process can typically have an acetylene concentration exceeding 100 ppmm to 2 mole %. The selective hydrogenation process can reduce the concentration of acetylene contained in the ethylene product feed to yield a reactor effluent or treated ethylene product having a reduced concentration of acetylene typically having a concentration significantly below 100 ppmm This process is highly selective in the hydrogenation of acetylene. The selectivity is typically greater than 70%. More typically, the selectivity is greater than 72%, and even greater than 74%. The ethylene selectivity is defined as the volume of ethylene in the reactor outlet effluent less the volume of ethylene in the reactor inlet feed divided by the difference of acetylene in the reactor inlet feed and acetylene in the reactor outlet effluent multiplied by 100.

The selective hydrogenation of acetylene is ethylene streams to form ethylene is usually carried out as a gas-phase process at a space velocity of the gaseous ethylene stream of from 500 v/vh to 15,000 v/vh, based on the catalyst volume, a temperature in the range of from 10° C. to 250° C., and a pressure of from 0.01 bar to 90 bar.

The molar ratio of hydrogen to acetylene in the feed that is contacted with the selective hydrogenation catalyst is typically in the range of from 0.8 to 1.8.

The selective hydrogenation of methylacetylene or propadiene, or both, contained in propylene streams to form propylene is usually carried out as a gas-phase process or a mixed gas-liquid phase process at a space velocity of the liquid propylene stream of from 1 v/vh to 50 v/vh, based on the catalyst volume, at a temperature in the range of from 10° C. to 180° C. and a pressure of from 0.01 bar to 50 bar. The molar ratio of hydrogen to methylacetylene and propadiene in the propylene stream in the feed that is contacted with the selective hydrogenation catalyst is typically in the range of from 0.8 to 2.

The following examples are provided to illustrate the invention, but they should not be construed as limiting it in any way.

EXAMPLE 1

This Example 1 describes the preparation of Catalyst 1 that is representative of the inventive catalyst.

In a 0.1 M solution of sodium dodecyl sulfate, $Pd(NO_3)_2$ and $AgNO_3$ are mixed in water and heated to 75° C. for 10 hrs. 400 g of an α-aluminum oxide support (tablets 4×4 mm) are impregnated with this mixture. The amount of metal salts is calculated to give 0.035 wt % Pd and 0.025 wt % Ag on the catalyst.

The impregnated carrier is dried in air at 120° C. for 2 hrs and calcined in a rotary kiln at 500° C. for 3 hrs.

EXAMPLE 2

This Example 2 describes the preparation of Catalyst 2 that is also representative of the inventive catalyst.

In a 0.1 M solution of sodium dodecyl sulfate, $Pd(NO_3)_2$ and $AgNO_3$ are mixed in water and heated to 80° C. for 10 hrs. 400 g of an α-aluminum oxide support (tablets 4×4 mm) are impregnated with this mixture. The amount of metal salts is calculated to give 0.035 wt % Pd and 0.040 wt % Ag on the catalyst.

The impregnated carrier is dried in air at 100° C. for 2 hrs and calcined in a rotary kiln at 500° C. for 3 hrs.

EXAMPLE 3

This Example 3 describes the preparation of comparative Catalyst 3, which is similar to the catalyst disclosed in PCT publication WO 2011/113881.

400 g of an α-aluminum oxide support (tablets 4×4 mm) was impregnated with an aqueous hydrazine solution (2% hydrazine content). The volume of the solution was equivalent to 35% of the total pore volume of the support. Subsequently, the support was impregnated with an aqueous solution of $AgNO_3$ and $Pd(NO_3)_2$. The concentrations of the noble metals in the solution were chosen to yield a palladium content of 0.035 wt % and a silver content of 0.025 wt % in the catalyst. The volume of the noble metal containing solution was equivalent to 65% of the total pore volume of the support.

The impregnated catalyst precursor was dried completely in a moving bed and, subsequently, calcined for five hours at a temperature of 630° C. under a nitrogen atmosphere.

EXAMPLE 4

This Example 4 describes the performance testing done to characterize the catalyst compositions of Examples 1-3.

Experimental conditions were chosen which closely resemble those of a first tail-end reactor of a steam cracker unit.

A laboratory reactor was filled with 15 ml of catalyst in five layers, diluted by 85 ml of α-alumina spheres. A feed having the composition presented in the following table was fed to the reactor at a rate providing a GHSV of 4,000 v/vh. The reactor was operated at a pressure of 10 bar and a temperature that was adjusted and maintained to provide 70% conversion of the acetylene, i.e., a 3,000 ppm acetylene concentration at the reactor outlet.

Feed Composition (in mole%)

| | |
|---|---|
| $C_2H_2$ (acetylene) | 1.0 (10,000 ppm) |
| $H_2$ | 1.0 |
| $C_2H_4$ (ethylene) | 30 |
| $C_3H_8$ (propane) | 1.0 |
| $N_2$ | Balance |

The following table presents results from the performance testing of the inventive catalysts and the comparison catalyst. Selectivity is calculated as follows: [(ethylene outlet concentration less ethylene inlet concentration)/(acetylene inlet concentration less acetylene outlet concentration)]*100.

Performance test results for the inventive and compartive catalysts

| Catalyst | % Selectivity of Catalyst After 150 hrs of Use | Change in Ethylene Selectivity from SOR After 150 hrs of Use | Increase in Reactor Temperature Required for 70% Acetylene Conversion After 150 hrs of Use |
|---|---|---|---|
| Catalyst 1 | 75.0 | −3.3 | 3° C. |
| Catalyst 2 | 74.8 | −2.3 | 2° C. |
| Catalyst 3 | 71.4 | −7.0 | 4° C. |

The performance data presented in the above table show that the inventive catalyst provides a significantly better acetylene conversion selectivity to ethylene than the comparative catalyst. This improvement in acetylene conversion selectivity provides for a higher ethylene yield and lower green oil yield with the use of the inventive catalyst when compared to the comparison catalyst.

The rate of decline in ethylene selectivity with use of the inventive catalyst is much lower than the rate of decline in ethylene selectivity with use of the comparative catalyst. Thus, the inventive catalyst is more stable and can provide a longer operating life than the comparative catalyst. The stability of the inventive catalyst is also demonstrated by the smaller rate of increase in the reactor temperature required for 70% acetylene conversion exhibited by the inventive catalyst relative to the comparative catalyst.

EXAMPLE 5

Figure 2:
FIG. 2 is a Transmission Electron Micrographic (TEM) image of the inventive catalyst showing the palladium/silver nanoparticles on alumina support.

This example presents FIG. 2, which is a transmission electron micrograph image of the inventive catalyst prepared as described in Example 1. The TEM scan has a magnification of x100,000 (200 kV), and it shows the alumina support of the catalyst with the bi-metallic nanoparticles residing on the surface of the alumina support. The arrows on the image point to the nanoparticles.

Figure 3:
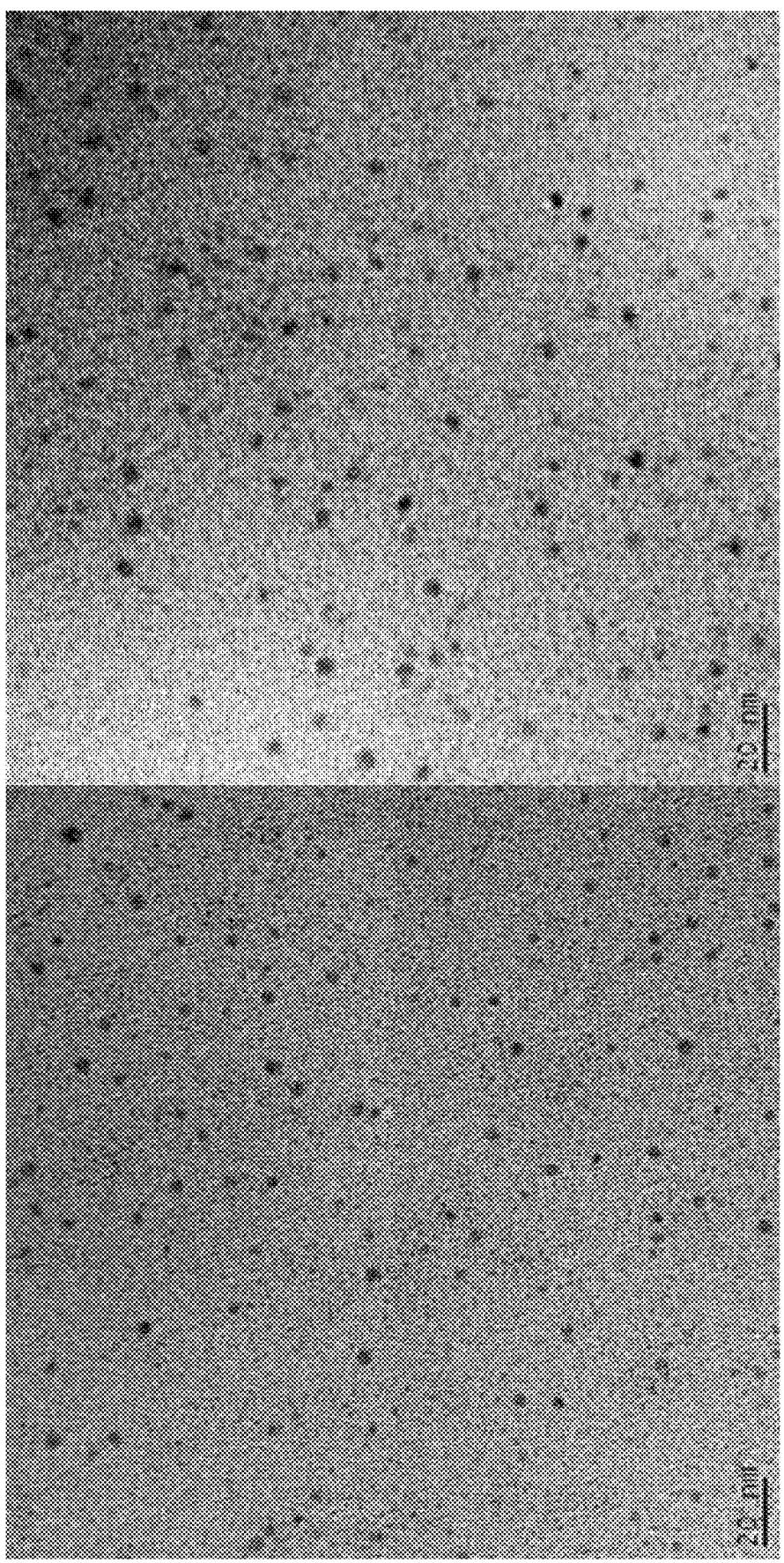
FIG. 3 is a Transmission Electron Micrographic (TEM) image of isolated and dried palladium/silver nanoparticles of the invention prepared in a micelle solution of the invention.

Also presented by this example is FIG. 3, which is a transmission electron micrograph image of the bi-metallic nanoparticles of the aqueous dispersion used in the preparation of the inventive catalyst. The TEM scan has a magnification of x100,000 (200 kV), and it shows the nanoparticles after drying the aqueous dispersion.

EXAMPLE 6

Figure 4:
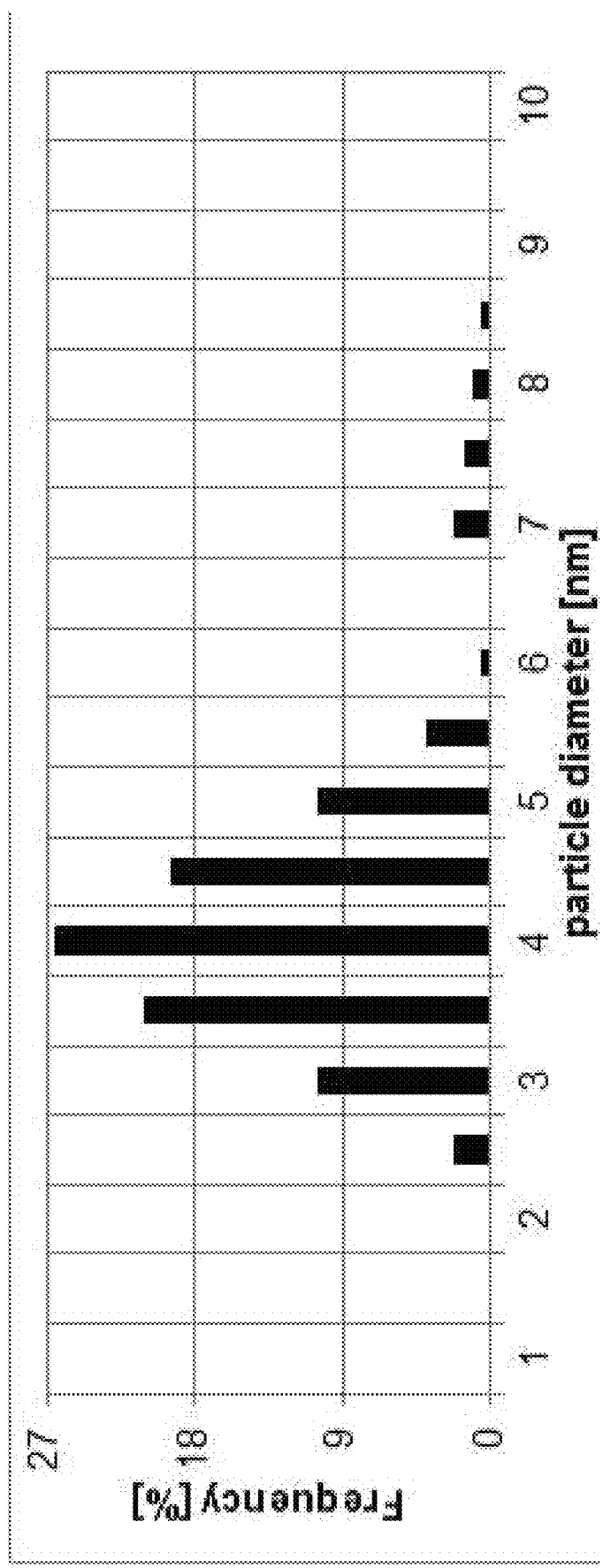
FIG. 4 presents a graph showing the size distribution of the palladium/silver nanoparticles of the invention in aqueous dispersion.

This example presents FIG. 4, which is an exemplary particle size distribution of the micelle stabilized nanoparticles in the aqueous dispersion. The particle size distribution was measured after mixing Pd(NO$_3$)$_2$ and AgNO$_3$ into a 0.1 M aqueous solution of sodium dodecyl sulfate (as described in examples 1 and 2) and stirring at 80° C. for 12 hrs. The Method applied is Dynamic Light Scattering.

That which is claimed is:

1. A method of making a composition useful as a selective hydrogenation catalyst or selective hydrogenation catalyst precursor, wherein the method comprises:
    providing an aqueous dispersion of bi-metallic nanoparticles formed by the reduction of a palladium salt and a silver salt in a mixture by the application of a surfactant;
    incorporating the aqueous dispersion into a carrier to provide an impregnated carrier; and
    drying the impregnated carrier followed by calcining the impregnated carrier in air at a calcination temperature to provide the composition, wherein the aqueous dispersion includes concentrations of silver and of palladium so that upon incorporation into the carrier and calcination of the impregnated carrier the composition comprises from 0.01 wt. % to 1 wt. % silver, based on the weight of the composition and silver as metal, and 0.01 wt. % to 1 wt. % palladium, based on the weight of the composition and palladium as metal.

2. The method as recited in claim 1, wherein the providing step comprises:
    mixing in water the palladium salt, the silver salt, and the surfactant to provide the mixture; and
    heating the mixture at a heating temperature and for a heating period sufficient to thereby provide the aqueous dispersion.

3. The method as recited in claim 2, wherein the heating temperature is in the range of from 30° C. up to 100° C. and the heating period is up to 24 hours.

4. The method as recited in claim 1, wherein the calcination temperature is in the range of from 250° C. to 600° C.

5. The method as recited in claim 1, wherein the silver salt is selected from the group of silver salts consisting of silver nitrate, silver halide, silver carbonate, silver phosphate, silver acetate, silver hydroxide, silver oxide, and silver sulfate.

6. The method as recited in claim 1, wherein the palladium salt is selected from the group of palladium salts consisting of palladium nitrate, palladium halide, palladium carbonate, palladium phosphate, palladium acetate, palladium oxide, and palladium sulfate.

7. The method as recited in claim 1, wherein the bi-metallic nanoparticles provide for a molar ratio of palladium-to-silver in the aqueous dispersion in the range of from 0.01:1 to 100:1 based on the total weight of the aqueous dispersion that includes both a continuous phase and a discontinuous phase.

8. The method as recited in claim 1, wherein the surfactant is selected from the group consisting of cationic surfactants, anionic surfactants, and nonionic surfactants.

9. The method as recited in claim 1, wherein the surfactant is selected from the group of anionic surfactants consisting of organo sulfate compounds, organo sulfite compounds, organo sulfonate compounds, organo phosphate compounds, and organo carboxylate compounds.

10. The method as recited in claim 1, wherein the surfactant is selected from the group of cationic surfactant compounds consisting of ammonium salts of primary amines, secondary amines, and tertiary amines.

11. The method as recited in claim 1, wherein the surfactant is selected from the group of nonionic surfactants consisting of ethoxylates, fatty alcohol ethoxylates, alkylphenol ethoxylates, and fatty acid esters.

12. The method as recited in claim 1, wherein the carrier is a shaped structure, comprising an inorganic oxide and having a shape selected from the group consisting of spheres, cylindrical pellets, and extrudates that are either cylinders or lobed shapes, wherein the spheres have a spherical diameter in the range of from 0.5 mm to 25 mm, the cylindrical pellets have a pellet diameter in the range of from 0.5 mm to 25 mm and a pellet length of from 1 mm to 50 mm, and the extrudates have an extrudate diameter in the range of from 0.5 mm to 25 mm, and an extrudate length in the range of from 1 mm to 50 mm, and wherein the shaped structure is defined as having an outer shell region and an interior region.

13. The method as recited in claim 12, wherein the incorporating step is either a wet impregnation or an incipient wetness impregnation providing for incorporation and concentration of the bi-metallic nanoparticles within the outer shell region having a depth in the range of from 1 micron to 400 microns.

14. The method as recited in claim 1, wherein the bi-metallic particles have a core-shell structure, and wherein the core is either palladium or silver.

15. A method of making a composition useful as a selective hydrogenation catalyst or selective hydrogenation catalyst precursor, wherein the method comprises:
   providing an aqueous dispersion of bi-metallic nanoparticles formed by the reduction of a palladium salt and a silver salt in a mixture by the application of a surfactant, wherein the bi-metallic nanoparticles provide for a molar ratio of palladium-to-silver in the aqueous dispersion in the range of from 0.01:1 to 100:1 based on the total weight of the aqueous dispersion that includes both a continuous phase and a discontinuous phase;
   incorporating the aqueous dispersion into a carrier to provide an impregnated carrier; and
   drying the impregnated carrier followed by calcining the impregnated carrier in air at a calcination temperature to provide the composition.

16. The method as recited in claim 15, wherein the providing step comprises:
   mixing in water the palladium salt, the silver salt, and the surfactant to provide the mixture; and
   heating the mixture at a heating temperature and for a heating period sufficient to thereby provide the aqueous dispersion.

17. The method as recited in claim 16, wherein the heating temperature is in the range of from 30° C. up to 100° C. and the heating period is up to 24 hours.

18. The method as recited in claim 15, wherein the calcination temperature is in the range of from 250° C. to 600° C.

19. The method as recited in claim 15, wherein the silver salt is selected from the group of silver salts consisting of silver nitrate, silver halide, silver carbonate, silver phosphate, silver acetate, silver hydroxide, silver oxide, and silver sulfate.

20. The method as recited in claim 15, wherein the palladium salt is selected from the group of palladium salts consisting of palladium nitrate, palladium halide, palladium carbonate, palladium phosphate, palladium acetate, palladium oxide, and palladium sulfate.

21. The method as recited in claim 15, wherein the surfactant is selected from the group consisting of cationic surfactants, anionic surfactants, and nonionic surfactants.

22. The method as recited in claim 15, wherein the surfactant is selected from the group of anionic surfactants consisting of organo sulfate compounds, organo sulfite compounds, organo sulfonate compounds, organo phosphate compounds, and organo carboxylate compounds.

23. The method as recited in claim 15, wherein the surfactant is selected from the group of cationic surfactant compounds consisting of ammonium salts of primary amines, secondary amines, and tertiary amines.

24. The method as recited in claim 15, wherein the surfactant is selected from the group of nonionic surfactants consisting of ethoxylates, fatty alcohol ethoxylates, alkylphenol ethoxylates, and fatty acid esters.

25. The method as recited in claim 15, wherein the carrier is a shaped structure, comprising an inorganic oxide and having a shape selected from the group consisting of spheres, cylindrical pellets, and extrudates that are either cylinders or lobed shapes, wherein the spheres have a spherical diameter in the range of from 0.5 mm to 25 mm, the cylindrical pellets have a pellet diameter in the range of from 0.5 mm to 25 mm and a pellet length of from 1 mm to 50 mm, and the extrudates have an extrudate diameter in the range of from 0.5 mm to 25 mm, and an extrudate length in the range of from 1 mm to 50 mm, and wherein the shaped structure is defined as having an outer shell region and an interior region.

26. The method as recited in claim 25, wherein the incorporating step is either a wet impregnation or an incipient wetness impregnation providing for incorporation and concentration of the bi-metallic nanoparticles within the outer shell region having a depth in the range of from 1 micron to 400 microns.

27. The method as recited in claim 15, wherein the aqueous dispersion includes concentrations of silver and of palladium so that upon incorporation into the carrier and calcination of the impregnated carrier the composition comprises from 0.01 wt. % to 1 wt. % silver, based on the weight of the composition and silver as metal, and 0.01 wt. % to 1 wt. % palladium, based on the weight of the composition and palladium as metal.

28. The method as recited in claim 15, wherein the bi-metallic particles have a core-shell structure, and wherein the core is either palladium or silver.

* * * * *